United States Patent
Bacqué et al.

(10) Patent No.: US 6,878,820 B2
(45) Date of Patent: Apr. 12, 2005

(54) STREPTOGRAMIN DERIVATIVES, THEIR PREPARATION AND COMPOSITIONS CONTAINING THEM

(75) Inventors: Eric Bacqué, Gif sur Yvette (FR); Jean-Claude Barrière, deceased, late of Gometz le Chatel (FR); by Françoise Tetot, legal representative, Bures sur Yvette (FR); Gérard Puchault, Marcilly (FR)

(73) Assignee: Aventis Pharma S. A., Antony Cedex (FR)

( * ) Notice: Subject to any disclaimer, the term of this patent is extended or adjusted under 35 U.S.C. 154(b) by 0 days.

(21) Appl. No.: 10/325,975

(22) Filed: Dec. 23, 2002

(65) Prior Publication Data
US 2003/0162962 A1 Aug. 28, 2003

Related U.S. Application Data
(60) Provisional application No. 60/353,953, filed on Feb. 5, 2002.

(30) Foreign Application Priority Data
Dec. 26, 2001 (FR) .............................................. 01 16856

(51) Int. Cl.[7] .................. C07D 498/18; A61K 31/4188
(52) U.S. Cl. ...................... 540/456; 540/457; 514/379; 514/380
(58) Field of Search ................ 540/456, 457; 514/379, 380

(56) References Cited

U.S. PATENT DOCUMENTS 5,242,938 A   9/1993   Lam ........................... 514/375

FOREIGN PATENT DOCUMENTS

GB   2206879 A   1/1989

*Primary Examiner*—Bruck Kifle
(74) *Attorney, Agent, or Firm*—Balaram Gupta

(57) ABSTRACT

The present invention relates to group A streptogramin derivatives of general formula (I) and processes for preparing the same:

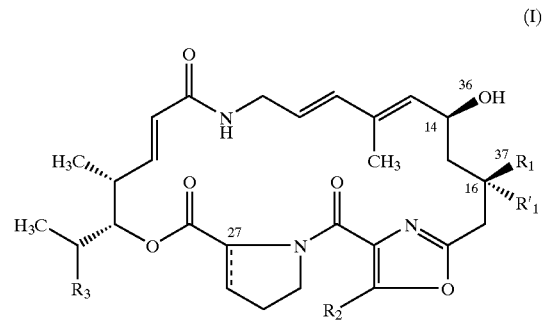

which has particularly advantageous antibacterial activity.

7 Claims, No Drawings

STREPTOGRAMIN DERIVATIVES, THEIR PREPARATION AND COMPOSITIONS CONTAINING THEM

Applicants claim the right to priority based on French Patent Application No. 0116856, filed Dec. 26, 2001, and the benefit of U.S. Provisional Application No. 60/353,953, filed Feb. 5, 2002.

The present invention relates to group A streptogramin derivatives of general formula:

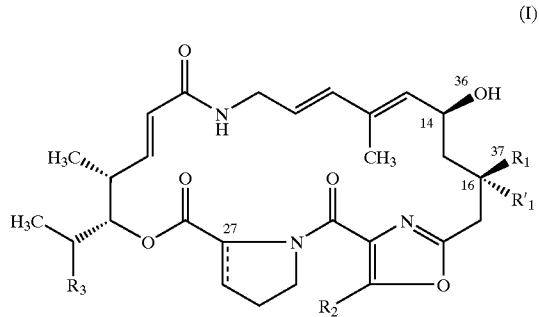

(I)

which has particularly advantageous antibacterial activity.

Among the known streptogramins, pristinamycin (RP 7293), an antibacterial agent of natural origin produced by *Streptomyces pristinaespiralis*, was isolated for the first time in 1955. The pristinamycin sold under the name Pyostacine® consists mainly of pristinamycin IIA combined with pristinamycin IA.

Another antibacterial agent of the streptogramin class: virginiamycin, was isolated from *Streptomyces virginiae*, ATCC 13161 [Antibiotics and Chemotherapy, 5, 632 (1955)]. The virginiamycin (Staphylomycine®) consists mainly of factor M1 (VM1) combined with factor S (VS).

F. Le Goffic et al., Eur J. Med. Chem. Chimica Therapeutica, 16(1), 69–72 (1981) has described the preparation of dihydroxy derivatives of pristinamycin IIA.

Patent application GB 2 206 879 discloses modified group A streptogramin derivatives of structure:

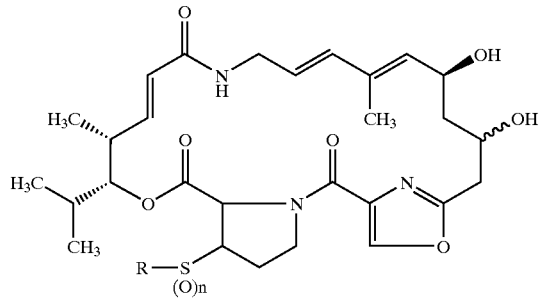

but these derivatives show only weak activity.

It has now been found that the group A streptogramin derivatives of general formula (I) in which:

R1 represents a halogen atom or a hydroxyl, alkyloxy, azido or thiocyanato radical, or R1 represents a radical —NR'R" for which R' is a hydrogen atom or a methyl radical and R" is a hydrogen atom or an alkyl, cycloalkyl, allyl, propynyl or benzyl radical, or —OR'", R'" being a hydrogen atom or an alkyl, cycloalkyl, allyl, propynyl or benzyl radical, or alternatively R" represents —NR°R°°, R° and R°° possibly representing a methyl radical, or forming, together with the nitrogen atom to which they are attached, a saturated or unsaturated 4- or 5-membered heterocycle also possibly containing another hetero atom chosen from nitrogen, oxygen and sulfur, and R'1 represents a hydrogen atom, or R1 and R'1 together form an oxo radical, R2 represents a halogen atom or an alkyl, alkenyl or alkynyl, phenyl or heteroaryl radical, or an alkylthio, phenylthio or heteroarylthio radical, R3 is a hydrogen atom or a methyl or ethyl radical, and the bond --- represents a single bond (27R stereochemistry) or a double bond, the alkyl radicals containing 1 to 6 carbons in a straight or branched chain and the alkenyl and/or alkynyl radicals containing 2 to 6 carbons in a straight or branched chain, have particularly advantageous antibacterial activity, especially on resistant bacterial microorganisms, alone or combined with a group B streptogramin derivative.

According to the invention, when R1 and/or R2 is a halogen atom, it may represent fluorine, chlorine, bromine or iodine;

when R2 is a heteroaryl or heteroarylthio radical, this radical is mono- or bicyclic and comprises 1 to 4 hetero atoms chosen from nitrogen, oxygen and sulfur.

By way of example, when R2 is a heteroaryl or heteroarylthio radical, the heteroaryl radical may be chosen from pyridyl, thienyl, furyl, pyrrolyl, imidazolyl, pyrazinyl, quinolyl, isoquinolyl, indolyl, oxazolyl, thiazolyl, pyrazolyl, indazolyl, thiadiazolyl or oxadiazolyl.

According to the invention, the streptogramin derivatives of general formula (I) may be prepared by metalation of a streptogramin derivative of general formula:

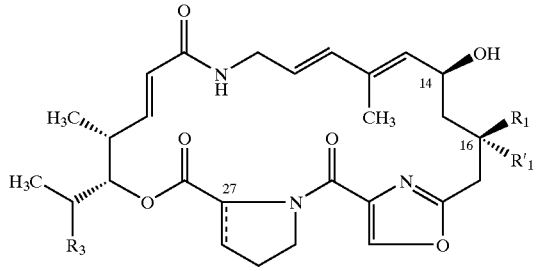

(II)

in which R'1, R3 and the bond --- are defined as above and R1 represents a fluorine atom or a hydroxyl or alkyloxy radical, or represents a radical —NR'R" for which R' is H or a methyl radical and R" is H or an alkyl, cycloalkyl, allyl, propynyl or benzyl radical, or —OR'", R'" being H, alkyl, cycloalkyl, allyl, propynyl or benzyl, or alternatively R" represents —NR°R°°, R° and R°° possibly being methyl, or forming, together with the nitrogen atom to which they are attached, a saturated or unsaturated 4- or 5-membered heterocycle also possibly containing another hetero atom chosen from nitrogen, oxygen and sulfur, or alternatively R1 and R'1 together form an oxo radical, by the action successively of an amide to give a polyanion corresponding, depending on the nature of the substituents and depending on whether the starting material is a streptogramin derivative of general formula (II) for which the bond --- is a double bond or a single bond, to the structures of general formulae:

3  4
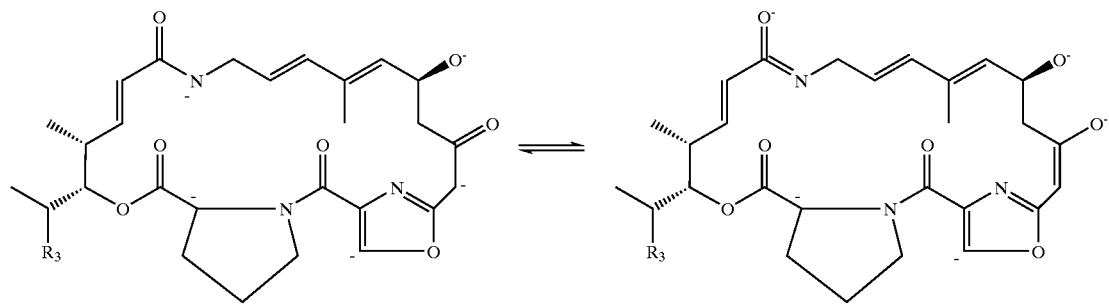
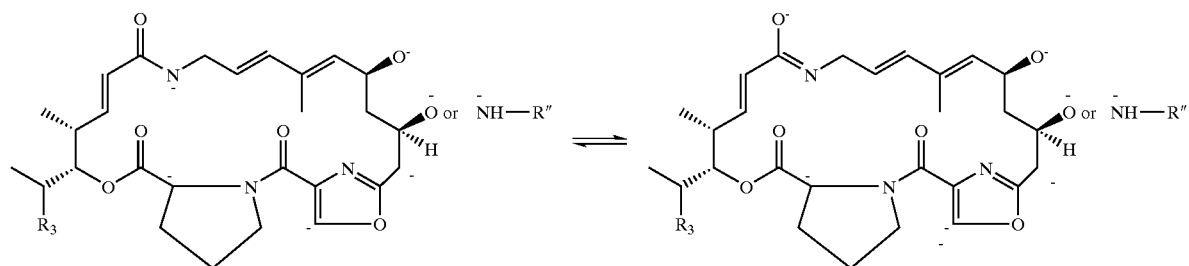
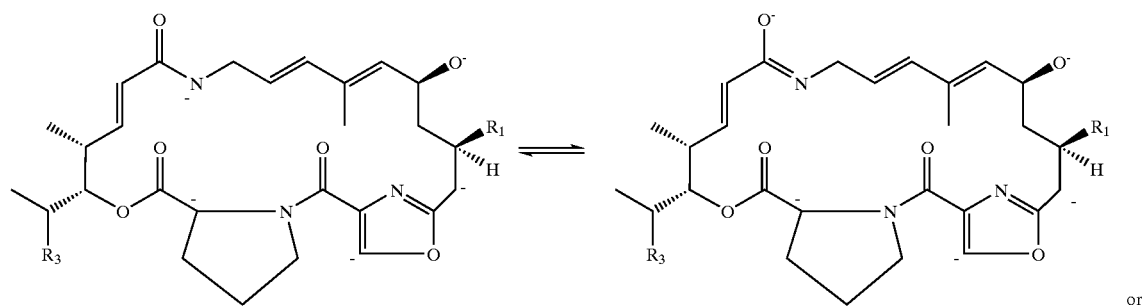
or

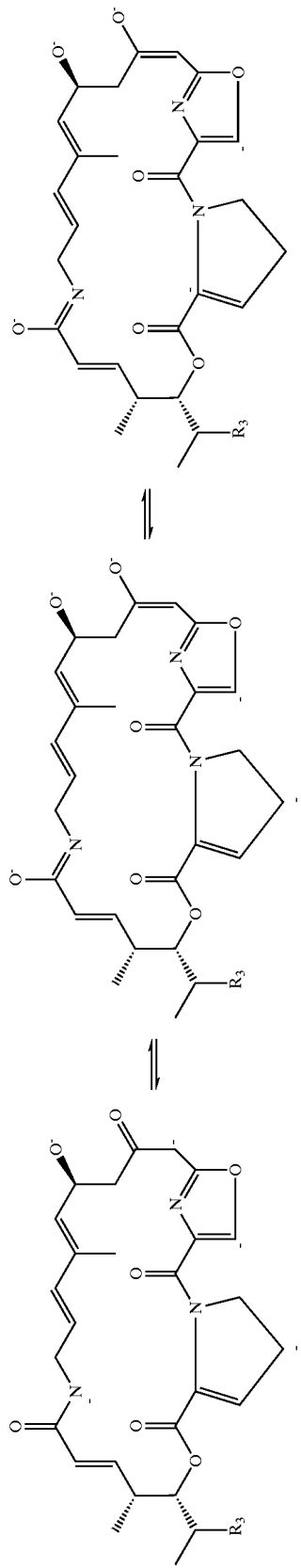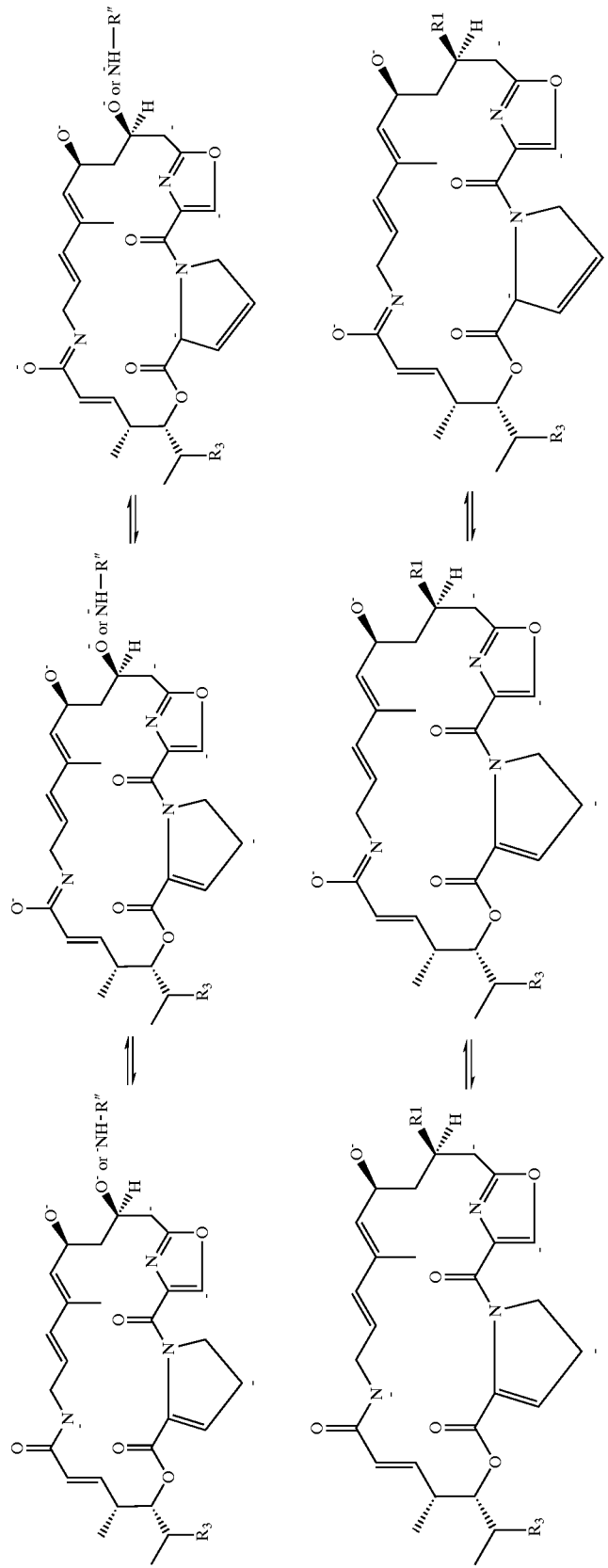

and for which R3 is defined as above, and R1 represents a fluorine atom or an alkyloxy radical, or represents a radical —NR'R" for which R' is a methyl radical and R" is an alkyl, cycloalkyl, allyl, propynyl or benzyl radical, or —OR'", R'" being H, alkyl, cycloalkyl, allyl, propynyl or benzyl, or alternatively R" represents —NR°R°°, R° and R°° possibly being methyl or forming, together with the nitrogen atom to which they are attached, a saturated or unsaturated 4- or 5-membered heterocycle also possibly containing another hetero atom chosen from nitrogen, oxygen and sulfur, and then by the action of an electrophilic agent which may be represented by the general formula:

R2-X  (III)

in which R2 is a halogen atom, an alkyl radical or an alkenyl or alkynyl radical, with the exception of representing a vinyl or ethynyl radical, and X represents a halogen atom or a sulfonyloxy radical, or alternatively by the action of a disulfide when R2 is alkylthio, phenylthio or heteroarylthio, followed, where appropriate, by the conversion of a streptogramin derivative of general formula (I) for which R2 is a chlorine, bromine or iodine atom, into a streptogramin derivative of general formula (I) for which R2 is a vinyl, ethynyl, phenyl or heteroaryl radical and/or, where appropriate, the streptogramin derivative of general formula (I) for which R1 and R'1 together form an oxo radical, is converted into a corresponding derivative for which R1 is a chlorine, bromine or iodine atom or an azido or thiocyanato radical and R'1 is a hydrogen atom, and/or followed by the conversion of a streptogramin derivative of general formula (I) for which the bond - - - is a double bond into a streptogramin derivative of general formula (I) for which the bond - - - is a single bond.

The metalation reaction is generally carried out at a temperature of between −100 and −20° C., in the presence of 4 to 7 equivalents of an amide, preferably a lithium amide chosen, for example, from lithium diisopropylamide and lithium 2,2,6,6-tetramethylpiperidine amide, in an anhydrous solvent, especially an ether such as, for example, anhydrous tetrahydrofuran, optionally in the presence of a co-solvent such as 1,3-dimethyl-3,4,5,6-tetrahydro-2(1H)-pyrimidinone or hexamethylphosphorotriamide, in the presence or absence of additives such as, for example, tetramethylethylenediamine, diazabicyclo[2.2.2]octane or anhydrous lithium chloride. It is advantageous to perform the process in inert medium, for example under argon.

The reaction of the electrophilic agent [represented especially by the general formula (III)] is carried out at a temperature of between −80 and 20° C. The electrophilic reagent is advantageously chosen from alkyl, allyl, propargyl, benzyl or heteroarylmethyl halides or sulfonates, or alternatively chosen from bromine, iodine or iodine chloride; it may also be chosen from halogen donors (N-bromosuccinimide or N-chlorosuccinimide, 1,1,2,2-tetrafluoro-1,2-dichloro- or -dibromoethane, 1,2-dibromo-1, 1,2,2-tetrachloroethane, 1,2-diiodoethane or 1,2-dibromoethane, 1-chloro-2-iodoethane or hexachloroacetone, for example). The process is advantageously performed in an organic solvent such as an ether, for example tetrahydrofuran.

The subsequent operation for conversion of a streptogramin derivative of general formula (I), for which R2 is chlorine, bromine or iodine, into a streptogramin derivative of general formula (I) for which R2 is vinyl, ethynyl, phenyl or heteroaryl is preferably carried out starting with a derivative for which the halogen is bromine or iodine, by the action of a tin derivative (vinyltributyltin or vinyltrimethyltin, for example) or of a boron derivative (for example boronic acid or a 9-borabicyclo[3.3.1]nonane derivative), or a zinc derivative (for example of structure R2ZnCl) in the presence of a catalyst such as a palladium derivative (for example tetrakis(triphenylphosphinepalladium) in the presence or absence of a phosphine (such as, for example, tetrakis (triphenylphosphine)), a base (such as, for example, a nitrogenous base: triethylamine, diethylamine or piperidine, or a carbonate: sodium or potassium carbonate) and optionally in the presence of a co-catalyst such as a copper salt (CuI), in an inert organic solvent, or a mixture of solvents such as an aromatic hydrocarbon (for example toluene), a nitrile (acetonitrile), an amide (such as, for example, dimethylformamide) or an ether (tetrahydrofuran) at a temperature of between 20° C. and the reflux point of the reaction mixture.

The subsequent operation for conversion of a streptogramin derivative of general formula (I), for which R1 and R'1 together form an oxo radical, into a corresponding derivative for which R1 is a chlorine, bromine or iodine atom or an azido or thiocyanato radical and R'1 is a hydrogen atom is carried out according to the application described in international patent application WO 01/02427, which is incorporated herein by way of reference.

When R1 and R'1 are defined as above with the exception of together representing an oxo radical, the subsequent operation for conversion of a streptogramin derivative of general formula (I) for which the bond - - - is a double bond into a streptogramin derivative of general formula (I) for which the bond - - - is a single bond (27R stereochemistry) is generally carried out by reduction using an alkali metal halide (for example sodium borohydride or lithium borohydride), in a solvent such as an ether (for example tetrahydrofuran), at a temperature of between 0 and 60° C. The separation of the 2 epimers at C27 is carried out according to the usual methods that do not adversely affect the rest of the molecule, especially by crystallization or chromatography.

The group A streptogramin derivatives of general formula (II), for which R1 is a fluorine atom or a radical —NR'R" for which R' is a hydrogen atom or a methyl radical and R" is a hydrogen atom or an alkyl, cycloalkyl, allyl, propynyl or benzyl radical, or —OR'", R'" being a hydrogen atom or an alkyl, cycloalkyl, allyl, propynyl or benzyl radical, or alternatively R" represents —NR°R°°, R° and R°° possibly representing a methyl radical or forming, together with the nitrogen atom to which they are attached, a saturated or unsaturated 4- or 5-membered heterocycle also possibly containing another hetero atom chosen from nitrogen, oxygen and sulfur, may be prepared according to or by analogy with the methods described in international patent applications WO 99/05165 and WO 01/02427.

The dihydroxy streptogramin derivative of general formula (II) may be obtained according to the methods described by F. Le Goffic et al., Eur J. Med. Chem. Chimica Therapeutica, 16(1), 69–72 (1981) or in patent application FR 2 795 733.

The separation of the 16R epimeric form and the 16S epimeric form is carried out according to the usual methods; for example, the separation of the epimeric forms may be carried out by chromatography, flash chromatography, high performance liquid chromatography (HPLC), on a chiral or achiral phase, or centrifuge partition chromatography (CPC), starting with the mixture of the 16R and 16S epimers or by crystallization.

The streptogramin derivatives of general formula (II) for which R1 is an alkyloxy radical may be prepared by the action of a derivative of general formula:

alk-X                                                     (V)

for which alk represents the corresponding alkyl radical and X represents a halogen atom, or a methylsulfonyloxy, p-toluenesulfonyloxy or trifluoromethylsulfonyloxy radical, in the presence of a phase-transfer agent, on a dihydroxy streptogramin derivative of general formula:

(VI)

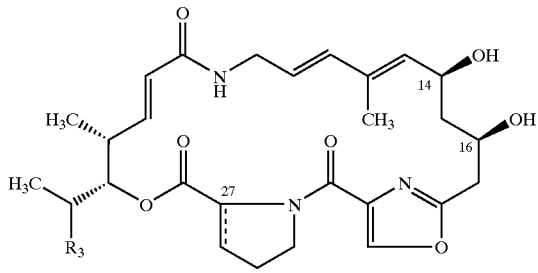

in which $R_3$ and the bond - - - are defined as above, and in which the hydroxyl function in position 14 and/or the amide function in position 8 have optionally been protected beforehand, followed, where appropriate, by removal of the protecting radical(s).

Preferably, when X is a halogen atom, a derivative of general formula (V) for which X is a bromine or iodine atom is reacted.

The phase-transfer agent is advantageously chosen from quaternary ammonium derivatives (for example tetraalkylammonium or trialkylbenzylammonium salts such as the chloride, bromide or sulfate).

The reaction is generally carried out in basic medium, for example in the presence of sodium or potassium hydroxide, or in the presence of potassium carbonate or cesium carbonate, at a temperature of between 10 and 60° C., in aqueous-organic medium, for example in a hydrocarbon (for example toluene), a halogenated solvent (for example dichloromethane) or an ester (especially ethyl acetate). The process is preferably performed at about 20° C. Preferably also, the process is performed in the presence of an excess of the derivative of general formula (V).

The protection and deprotection of the hydroxyl radical in position 14 or of the amide in position 8 are carried out according to the usual methods that do not affect the rest of the molecule, especially by applying the methods described by T. W. Greene and P. G. M. Wuts, Protective Groups in Organic Synthesis (2nd edition), A. Wiley—Interscience Publication (1991) or by McOmie, Protective Groups in Organic Chemistry, Plenum Press (1973). For example, the protection of the hydroxyl radical is carried out with an allylic radical, which is installed and removed according to the known methods. The protection of the amide may be carried out especially with the t-butoxycarbonyl radical.

When the reaction leads to a mixture of the 14- and 16-O-alkyl isomers, these isomers may be separated according to the usual methods that do not adversely affect the rest of the molecule, especially by chromatography [High Performance Liquid Chromatography (HPLC) on a normal or reverse phase, on a chiral or achiral phase or by flash chromatography] or by crystallization.

The pristinamycin derivatives of general formula (IV) correspond, respectively, to pristinamycin IIA (PIIA), pristinamycin IIB (PIIB), pristinamycin IIC (PIIC), pristinamycin IID (PIID), pristinamycin IIF (PIIF) and pristinamycin IIG (PIIG), which are known components of natural pristinamycin. The components PIIF and PIIG have been described in European patent EP 614 910. Pristinamycin IIC (PIIC) and pristinamycin IID (PIID) may be obtained as described by J. C. Barrière et al., Expert. Opin. Invest. Drugs, 3(2), 115–31 (1994).

The preparation and separation of the natural group A streptogramin components [streptogramins of general formula (IV)] is carried out by fermentation and isolation of the constituents from the fermentation must according to or by analogy with the method described by J. Preud'homme et al., Bull. Soc. Chim. Fr., vol. 2, 585 (1968) or in European patent EP 614 910. Alternatively, the preparation of the natural group A components may be carried out by specific fermentation, as described in patent application FR 2 689 518.

The streptogramin derivatives of general formula (I) may be purified, where appropriate, by physical methods such as crystallization, chromatography or CPC.

The streptogramin derivatives of general formula (I) for which R1 represents a radical —NR'R" may be converted into the form of addition salts with acids, by the known methods. It is understood that these salts, when they exist, also fall within the context of the present invention.

As examples of addition salts with pharmaceutically acceptable acids, mention may be made of the salts formed with mineral acids (hydrochlorides, hydrobromides, sulfates, nitrates and phosphates) or with organic acids (succinates, fumarates, tartrates, acetates, propionates, maleates, citrates, methanesulfonates, ethanesulfonates, phenylsulfonates, p-toluenesulfonates, isethionates, naphthylsulfonates or camphorsulfonates, or with substitution derivatives of these compounds).

It is understood that the combinations formed by means of the derivatives according to the invention and the group B streptogramins also fall within the context of the present invention.

The streptogramin derivatives according to the present invention have antibacterial properties and synergizing properties on the antibacterial activity of the group B streptogramin derivatives. They are particularly advantageous on account of their powerful activity alone or in combination.

When they are combined with a group B streptogramin component or derivative, this component or derivative may be chosen, depending on whether it is desired to obtain a form for oral or parenteral administration, from the natural components: pristinamycin IA, pristinamycin IB, pristinamycin IC, pristinamycin ID, pristinamycin IE, pristinamycin IF, pristinamycin IG, virginiamycin S1, S3 or S4, vernamycin B or C, and etamycin, or from semisynthetic derivatives as described in patents or patent applications U.S. Pat. Nos. 4,618,599, 4,798,827, 5,326,782, 5,786,449, WO 01/10895, WO 01/07467, EP 772 630, EP 770 132 or EP 1 056 071.

The streptogramin derivatives according to the present invention have antibacterial properties and synergizing properties on the antibacterial activity of group B streptogramin derivatives, especially on *Staphylococcus epidermidis* N52 or on resistant strains such as *Staphylococcus aureus* Stephan. They are particularly advantageous on account of their powerful activity alone or in combination.

In vitro on *Staphylococcus epidermidis* N52, the streptogramin derivatives according to the invention have been found to be active at concentrations of between 1 and 64 μg/ml alone or between 0.25 and 32 μg/ml combined with a group B derivative such as pristinamycin IB. In vitro on *Staphylococcus aureus* Stephan, they have been found to be active at concentrations of between 0.5 and 64 µg/ml.

Finally, the products according to the invention have shown no toxicity.

The examples which follow, given in a nonlimiting manner, illustrate the present invention.

In the examples which follow, the nomenclature 16-deoxopristinamycin IIA (or IIB) means the replacement of the ketone function in position 16 with two hydrogen atoms. As the chromatography proceeds, all the fractions are analyzed by thin layer chromatography (TLC), on Merck 60F254 silica plates. The fractions corresponding to the same spot on TLC are combined and then concentrated to dryness under reduced pressure (30° C.; 2.7 kPa). The residues thus obtained are analyzed by the usual spectroscopic techniques (NMR; IR; MS), thus allowing the expected product to be identified.

EXAMPLE 1

(16R)-20-Bromo-16-deoxo-16-fluoropristinamycin IIB

A solution of lithium diisopropylamide, cooled to −50° C., is added over one hour to 5.32 g of (16R)-16-deoxo-16-fluoropristinamycin IIB dissolved in 100 cm$^3$ of anhydrous tetrahydrofuran, at −72° C. under an argon atmosphere. The lithium diisopropylamide solution was prepared beforehand by adding, at −50° C., 31 cm$^3$ of n-butyllithium (1.6 M in hexane) to a solution of 100 cm$^3$ of tetrahydrofuran and 7 cm$^3$ of diisopropylamine, followed by warming to 20° C. after the addition. 7.5 cm$^3$ of tetramethylethylenediamine are quickly added to the resulting thick brown solution, maintained at −72° C. After stirring the reaction mixture for ten minutes at −72° C., 9.8 g of 1,2-dibromo-1,1,2,2-tetrachloroethane dissolved in 20 cm$^3$ of tetrahydrofuran are added over fifteen minutes, still at −72° C. The mixture is stirred for 1 hour at −72° C., followed by dropwise addition of 10 cm$^3$ of acetic acid and then 100 cm$^3$ of water. The solution obtained, warmed to 20° C., is concentrated under reduced pressure. The residue is taken up in 100 cm$^3$ of water and 100 cm$^3$ of ethyl acetate. The organic phase is separated out and the aqueous phase is extracted with 100 cm$^3$ of ethyl acetate. The combined organic phases are washed with 50 cm$^3$ of water containing 1N hydrochloric acid so as to adjust the pH of the aqueous phase to 2. The resulting organic phase is separated out, washed successively with 50 cm$^3$ of water, with aqueous 5% sodium bicarbonate solution and with 50 cm$^3$ of brine and then dried over sodium sulfate, filtered and concentrated to dryness under reduced pressure (2.7 kPa) to give 10.3 g of an orange-colored foam. This residue is purified by two successive flash chromatographies on silica [eluent: ethyl acetate/cyclohexane (70/30 by volume) and then dichloromethane/methanol (97/3 by volume)]. After concentration under reduced pressure (2.7 kPa) of the fractions containing the expected product, 0.53 g of (16R)-20-bromo-16-deoxo-16-fluoropristinamycin IIB is obtained in the form of a pale yellow powder melting at about 172° C.

1H NMR spectrum (400 MHz, CDCl$_3$, δ in ppm): 0.96 (d, J=6.5 Hz: 3H); 1.00 (d, J=6.5 Hz: 3H); 1.12 (d, J=6.5 Hz: 3H); from 1.55 to 2.15 (mt: 5H); 1.81 (s: 3H); 2.16 (mt: 1H); 2.27 (mt: 1H); 2.77 (mt: 1H); 2.91 (ddd, J=26–17 and 5 Hz: 1H); 3.18 (doubled t, J=17 and 7 Hz: 1H); 3.48 (mt: 1H); 3.65 (mt: 1H); 4.06 (mt: 1H); 4.58 (mt: 1H); 4.81 (dd, J=10 and 1.5 Hz: 1H); from 4.80 to 4.90 (mt: 1H); 4.87 (dd, J=9 and 4 Hz: 1H); 5.12 (dmt, JHF=48 Hz: 1H); 5.43 (broad d, J=9 Hz: 1H); 5.71 (ddd, J=16–8.5 and 4 Hz: 1H); 5.83 (dd, J=16 and 1.5 Hz: 1H); 5.94 (mt: 1H); 6.24 (d, J=16 Hz: 1H); 6.53 (dd, J=16 and 5 Hz: 1H).

EXAMPLE 2

(16R)-16-Deoxo-16-fluoro-20-methylpristinamycin IIB 0.87 cm$^3$ of lithium borohydride (2 M in tetrahydrofuran) is added rapidly to a solution, cooled to 0° C., of 0.76 g of (16R)-16-deoxo-16-fluoro-20-methylpristinamycin IIA in 20 cm$^3$ of tetrahydrofuran. After addition, the reaction mixture is stirred at 0° C. for 3.5 hours, followed by addition of 10 cm$^3$ of 1N hydrochloric acid and 10 cm$^3$ of water. The pH of the mixture obtained is adjusted to 6.7 by addition of aqueous sodium bicarbonate solution. The mixture is extracted with twice 35 cm$^3$ of dichloromethane. The organic phases are combined and then washed with 30 cm$^3$ of brine, dried over sodium sulfate, filtered and concentrated to dryness under reduced pressure (2.7 kPa) to give 0.63 g of a white foam, which is purified by semi-preparative HPLC [Kromasil C8 10 µm phase; eluent: water/acetonitrile (60/40 by volume)]. The fractions containing the expected product are extracted with twice 30 cm$^3$ of dichloromethane. The organic phases are combined and then dried over sodium sulfate, filtered and concentrated to dryness under reduced pressure (2.7 kPa) to give 0.145 g of a white solid. This solid is stirred for 1 hour in a pentane/diisopropyl ether mixture, filtered off and then dried overnight under reduced pressure (2.7 kPa) to give 0.12 g of (16R)-16-deoxo-16-fluoro-20-methylpristinamycin IIB, in the form of a white powder melting at about 137° C.

1H NMR spectrum (400 MHz, CDCl$_3$, δ in ppm): 0.96 (d, J=6.5 Hz: 3H); 1.00 (d, J=6.5 Hz: 3H); 1.11 (d, J=6.5 Hz: 3H); 1.65 (d, J=3.5 Hz: 1H); from 1.65 to 2.05 (mt: 5H); 1.81 (s: 3H); 2.13 (mt: 1H); 2.22 (mt: 1H); 2.53 (s: 3H); 2.76 (mt: 1H); 2.86 (ddd, J=24–17 and 5 Hz: 1H); 3.12 (doubled t, J=17 and 7 Hz: 1H); 3.48 (ddd, J=16–9 and 3 Hz: 1H); 3.73 (mt: 1H); 4.08 (mt: 1H); 4.55 (broad ddd, J=16–9 and 3Hz: 1H); 4.81 (dd, J=10 and 2 Hz: 1H); from 4.80 to 4.90 (mt: 1H); 4.85 (dd, J=9 and 3.5 Hz: 1H); 5.12 (dmt, JHF=48 Hz: 1H); 5.42 (broad d, J=9 Hz: 1H); 5.70 (ddd, J=16–9 and 4 Hz: 1H); 5.82 (dd, J=16 and 2 Hz: 1H); 5.94 (mt: 1H); 6.23 (broad d, J=16 Hz: 1H); 6.52 (dd, J=16 and 5 Hz: 1H).

(16R)-16-Deoxo-16-fluoro-20-methylpristinamycin IIA may be obtained in the following manner.

A solution of lithium diisopropylamide, cooled to −50° C., is added over one hour to 10.6 g of (16R)-16-deoxo-16-fluoropristinamycin IIA in 300 cm$^3$ of anhydrous tetrahydrofuran and 20 cm$^3$ of 1,3-dimethyl-3,4,5,6-tetrahydro-2 (1H)-pyrimidinone at −72° C. under an argon atmosphere. (The lithium diisopropylamide solution was prepared beforehand by adding, at −30° C., 50 cm$^3$ of n-butyllithium (1.6 M in hexane) to a solution of 100 cm$^3$ of tetrahydrofuran and 11.2 cm$^3$ of diisopropylamine, followed by warming to 20° C. after the addition). 12.1 cm$^3$ of tetramethylethylenediamine are added rapidly to the resulting thick brown solution, maintained at −72° C. After stirring the reaction mixture for ten minutes at −72° C., 12.4 g of methyl iodide are added over five minutes, still at −72° C. The mixture is stirred for 1 hour at −72° C., followed by dropwise addition of 12.6 cm$^3$ of acetic acid and then 60 cm$^3$ of water. The solution obtained, warmed to 20° C., is concentrated under reduced pressure. The thick brown oil obtained is taken up in 200 cm$^3$ of water and 500 cm$^3$ of ethyl acetate. Concentrated hydrochloric acid (10 cm$^3$) is added so as to adjust the pH of the aqueous phase to 3. The organic phase is separated out and the aqueous phase is extracted with 200 cm$^3$ of ethyl acetate. The combined organic phases are washed with 200 cm$^3$ of water containing sodium bicarbonate so as to obtain a final pH of 7–8. The resulting organic phase is separated out, washed with 100 cm$^3$ of brine and then dried over sodium sulfate, filtered and concentrated to dryness under reduced pressure (2.7 kPa) to give 15.1 g of a brown oil, which is purified by two successive flash chromatographies [eluent: ethyl acetate/cyclohexane (50/50 by volume) and then dichloromethane/methanol/acetonitrile (94/3/3 by volume)]. After concentration under reduced pressure (2.7 kPa), 1 g of (16R)-16-deoxo-16-fluoro-20-methylpristinamycin IIA is obtained in the form of a white powder melting at about 178° C.

1H NMR spectrum (400 MHz, CDCl$_3$, δ in ppm): 0.99 (d, J=6.5 Hz: 6H); 1.13 (d, J=6.5 Hz: 3H); 1.52 (d, J=4 Hz: 1H); 1.75 (s: 3H); from 1.95 to 2.20 (mt: 2H); 2.27 (mt: 1H); 2.41 (s: 3H); from 2.60 to 2.90 (mt: 3H); 2.97 (mt: 1H); 3.18 (doubled t, J=14.5 and 3.5 Hz: 1H); 3.85 (very broad d, J=18 Hz: 1H); 4.08 (mt: 1H); 4.29 (mt: 2H); from 4.40 to 4.70 (mt: 1H); 4.62 (mt: 1H); 4.94 (mt: 2H); 5.66 (dt, J=16 and 4 Hz: 1H); 5.91 (broad d, J=16 Hz: 1H); 5.99 (broad d, J=16 Hz: 1H); 6.14 (t, J=3 Hz: 1H); 6.59 (dd, J=16 and 7 Hz: 1H); 7.07 (multiplet: 1H).

EXAMPLE 3

(16R)-16-Deoxo-16-dimethylamino-20-methylpristinamycin IIB

A solution of lithium diisopropylamide is added dropwise to a solution of 1 g of (16R)-16-deoxo-16-dimethylaminopristinamycin IIA in 40 cm$^3$ of anhydrous tetrahydrofuran, at −75° C. under an argon atmosphere. The lithium diisopropylamide solution was prepared beforehand by adding, at −15° C., 5.6 cm$^3$ of n-butyllithium (1.6 M in hexane) to a solution of 10 cm$^3$ of tetrahydrofuran and 1.26 cm$^3$ of diisopropylamine. The resulting dark brown solution is stirred for 5 minutes at −70° C., followed by dropwise addition of 0.56 cm$^3$ of methyl iodide. After addition, the mixture is stirred for 5 minutes at −70° C., followed by addition of 50 cm$^3$ of water and 7 cm$^3$ of aqueous 10% phosphoric acid solution. The mixture obtained, warmed to 20° C., is extracted with 3 times 75 cm$^3$ of ethyl acetate. The combined organic phases are washed with 75 cm$^3$ of brine and then dried over sodium sulfate, filtered and concentrated to dryness under reduced pressure (2.7 kPa) to give 0.94 g of a yellow solid, which is purified by preparative HPLC [Kromasil C8®, 10 μm; eluent: water/acetonitrile (72.5/27.5 by volume) containing 0.1% trifluoroacetic acid]. After concentration of the fractions containing the expected product under reduced pressure (2.7 kPa), a white foam is obtained, which is stirred in 20 cm$^3$ of diisopropyl ether and then filtered. The solid obtained is dried under reduced pressure (2.7 kPa) to give 0.15 g of (16R)-16-deoxo-16-dimethylamino-20-methylpristinamycin IIA in the form of a white powder melting at about 145° C.

1H NMR spectrum (400 MHz, CDCl$_3$, δ in ppm): 0.98 (d, J=6.5 Hz: 3H); 0.99 (d, J=6.5 Hz: 3H); 1.13 (d, J=6.5 Hz: 3H); 1.69 (s: 3H); 1.76 (mt: 1H); from 1.95 to 2.10 (mt: 2H); from 2.35 to 2.50 (mt: 1H); 2.35 (s: 9H); 2.49 (t, J=12 Hz: 1H); from 2.60 to 2.75 (mt: 2H); from 2.80 to 2.90 (mt: 1H); 2.89 (broad d, J=12 Hz: 1H); 3.68 (very broad d, J=18 Hz: 1H); 4.07 (mt: 1H); 4.33 (mt: 1H); 4.40 (mt: 1H); 4.52 (multiplet: 1H); 4.82 (broad d, J=9 Hz: 1H); 4.95 (dd, J=10 and 1.5 Hz: 1H); 5.63 (ddd, J=16–5 and 3.5 Hz: 1H); 5.88 (broad d, J=16 Hz: 1H); 6.05 (broad d, J=16 Hz: 1H); 6.12 (t, J=3 Hz: 1H); 6.51 (dd, J=16 and 8 Hz: 1H); 7.48 (multiplet: 1H).

EXAMPLE 4

(16R)-20-Bromo-16-deoxo-16-fluoropristinamycin IIA

Working as in Example 1, but starting with 10.6 g of (16R)-16-deoxo-16-fluoropristinamycin IIA in 100 cm$^3$ of anhydrous tetrahydrofuran, to which is added over 45 minutes a solution of lithium diisopropylamide (prepared beforehand from 50 cm$^3$ of n-butyllithium, 300 cm$^3$ of tetrahydrofuran and 11.2 cm$^3$ of diisopropylamine), 12.1 cm$^3$ of tetramethylethylenediamine and 39 g of 1,1-dibromo-1,1,2,2-tetrachloroethane in 100 cm$^3$ of tetrahydrofuran added over 15 minutes. After aqueous work-up, 43 g of a brown oil are obtained, and are stirred for 48 hours in the presence of diisopropyl ether. The resulting suspension is filtered and then dried to give 15 g of an orange-colored residue, which is purified by two successive flash chromatographies [eluent: dichloromethane/methanol/acetonitrile (94/3/3 by volume) and then ethyl acetate/cyclohexane (70/30 by volume)]. After concentration under reduced pressure (2.7 kPa) of the fractions containing the expected product, a solid is obtained, which is stirred in 30 cm$^3$ of ethyl ether, filtered off and then dried under reduced pressure (2.7 kPa) to give 1.9 g of (16R)-20-bromo-16-deoxo-16-fluoropristinamycin IIA, in the form of a pale yellow powder melting at about 105° C.

1H NMR spectrum (400 MHz, CDCl$_3$, δ in ppm): 0.97 (d, J=6.5 Hz: 3H); 0.99 (d, J=6.5 Hz: 3H); 1.12 (d, J=6.5 Hz: 3H); 1.53 (d, J=3 Hz: 1H); 1.75 (s: 3H); from 1.90 to 2.15 (mt: 2H); 2.30 (dddd, J=30–16–5 and 3 Hz: 1H); from 2.60 to 2.80 (mt: 2H); 2.83 (mt: 1H); 3.02 (ddd, J=14–10 and 7.5 Hz: 1H); 3.22 (doubled t, J=14 and 3 Hz: 1H); 3.90 (broad d, J=20 Hz: 1H); 4.05 (mt: 1H); 4.26 (mt: 1H); from 4.25 to 4.40 (multiplet: 1H); 4.53 (d multiplet, JHF=48 Hz: 1H); 4.64 (mt: 1H); from 4.90 to 5.00 (mt: 1H); 4.93 (dd, J=10 and 1.5 Hz: 1H); 5.69 (dt, J=16 and 4 Hz: 1H); 5.90 (broad d, J=16 Hz: 1H); 6.01 (broad d, J=16 Hz: 1H); 6.19 (t, J=3 Hz: 1H); 6.60 (dd, J=16 and 7.5 Hz: 1H); 7.18 (multiplet: 1H).

EXAMPLE 5

(16R)-16-Deoxo-16-fluoro-20-vinylpristinamycin IIB 0.62 cm$^3$ of vinyltributyltin and then 25 mg of tetrakis(triphenylphosphine)palladium are rapidly added to a solution of 0.7 g of (16R)-16-deoxo-16-fluoro-20-iodopristinamycin IIB in a mixture of 21 cm$^3$ of toluene and 2.1 cm$^3$ of N,N-dimethylformamide at 20° C. and under argon. The brown solution obtained is heated at 80° C. for 20 hours. The reaction mixture is filtered through Clarcel® and the filtrate obtained is diluted by adding 50 cm$^3$ of ethyl acetate. The solution obtained is washed with twice 30 cm$^3$ of water and then with 30 cm$^3$ of brine. The organic phase is dried over magnesium sulfate, filtered and then concentrated under reduced pressure (2.7 kPa) to give a solid residue, which is purified by flash chromatography on silica [eluent: dichloromethane/methanol (97/3 by volume)]. After concentration under reduced pressure (2.7 kPa) of the fractions containing the expected product, a solid is obtained, which is stirred in 30 cm$^3$ of ethyl ether and then filtered off and dried under reduced pressure (2.7 kPa) to give 0.22 g of (16R)-16-deoxo-16-fluoro-20-vinylpristinamycin IIB in the form of a beige-colored powder melting at about 160° C.

1H NMR spectrum (400 MHz, CDCl$_3$, δ in ppm): 0.96 (d, J=6.5 Hz: 3H); 1.00 (d, J=6.5 Hz: 3H); 1.11 (d, J=6.5 Hz: 3H); 1.66 (d, J=3.5 Hz: 1H); from 1.70 to 2.05 (mt: 5H); 1.82 (s: 3H); 2.15 (mt: 1H); 2.25 (mt: 1H); 2.76 (mt: 1H); 2.92 (ddd, J=24–17 and 5 Hz: 1H); 3.18 (doubled t, J=17 and 7 Hz: 1H); 3.48 (mt: 1H); 3.73 (mt: 1H); 4.09 (mt: 1H); 4.56 (mt: 1H); 4.80 (dd, J=10 and 1.5 Hz: 1H); from 4.80 to 4.90 (mt: 1H); 4.85 (dd, J=9 and 3.5 Hz: 1H); 5.15 (dmt, JHF=48 Hz: 1H); from 5.40 to 5.50 (mt: 1H); 5.42 (dd, J=11 and 1 Hz: 1H); 5.70 (ddd, J=16–9.5 and 4 Hz: 1H); 5.83 (dd, J=16 and 1.5 Hz: 1H); 5.85 (dd, J=18 and 1 Hz: 1H); 5.93 (broad d, J=9.5 Hz: 1H); 6.24 (broad d, J=16 Hz: 1H); 6.52 (dd, J=16 and 4 Hz: 1H); 7.13 (dd, J=18 and 11 Hz: 1H).

(16R)-16-Deoxo-16-fluoro-20-iodopristinamycin IIB may be obtained in the following manner.

A solution of lithium diisopropylamide, cooled to −70° C., is added over one hour to 2.66 g of (16R)-16-deoxo-16-fluoropristinamycin IIB dissolved in 50 cm$^3$ of anhydrous tetrahydrofuran, at −70° C. under an argon atmosphere. (The lithium diisopropylamide solution was prepared beforehand by adding, at −40° C., 12.4 cm$^3$ of n-butyllithium (1.6 M in hexane) to a solution of 50 cm$^3$ of tetrahydrofuran and 2.8 cm$^3$ of diisopropylamine, followed by warming to 20° C. over 5 minutes). 3 cm$^3$ of tetramethylethylenediamine are added over 5 minutes to the resulting orange solution, maintained at −72° C. After stirring the reaction mixture for 5 minutes at −70° C., 1.27 g of iodine dissolved in 10 cm$^3$ of tetrahydrofuran are added over 10 minutes, still at −70° C. The mixture is stirred for 15 minutes at −72° C., followed by dropwise addition of 5 cm$^3$ of acetic acid and then 10 cm$^3$ of water once the reaction mixture has returned to 0° C. The mixture obtained is taken up in 800 cm$^3$ of water and 300 cm$^3$ of ethyl acetate. The organic phase is separated out and the aqueous phase is extracted with 300 cm$^3$ of ethyl acetate. The combined organic phases are washed with 300 cm$^3$ of water containing 1N hydrochloric acid so as to adjust the pH of the aqueous phase to 2 after washing. The resulting organic phase is separated out, washed successively with 50 cm$^3$ of water, with aqueous 5% sodium bicarbonate solution and with 50 cm$^3$ of brine and then dried over sodium sulfate, filtered and concentrated to dryness under reduced pressure (2.7 kPa) to give a brown solid, which is combined with two other batches obtained under similar conditions. This mixture (8.3 g) is purified by flash chromatography on silica [eluent: dichloromethane/methanol (97/3 by volume)]. After concentration under reduced pressure (2.7 kPa), 0.75 g of (16R)-16-deoxo-16-fluoro-20-iodopristinamycin IIB is obtained in the form of an amorphous yellow powder, which is used without further purification.

1H NMR spectrum (400 MHz, CDCl$_3$, δ in ppm): 0.94 (d, J=6.5 Hz: 3H); 1.00 (d, J=6.5 Hz: 3H); 1.11 (d, J=6.5 Hz: 3H); from 1.55 to 2.05 (mt: 5H); 1.80 (s: 3H); 2.15 (mt: 1H); 2.25 (mt: 1H); 2.75 (mt: 1H); 2.93 (ddd, J=26–17 and 5 Hz: 1H); 3.21 (doubled t, J=17 and 7.5 Hz: 1H); 3.48 (mt: 1H); 3.63 (mt: 1H); 4.07 (mt: 1H); 4.56 (mt: 1H); 4.79 (dd, J=10 and 1.5 Hz: 1H); from 4.80 to 4.90 (mt: 1H); 4.89 (dd, J=9 and 4 Hz: 1H); 5.11 (d mt, JHF=48 Hz: 1H); 5.42 (broad d, J=9 Hz: 1H); 5.70 (ddd, J=16–9 and 4 Hz: 1H); 5.82 (dd, J=16 and 2 Hz: 1H); 5.92 (dd, J=9 and 2.5 Hz: 1H); 6.24 (broad d, J=16 Hz: 1H); 6.52 (dd, J=16 and 5 Hz: 1H).

EXAMPLE 6

20-Methylpristinamycin IIA 5.9 cm$^3$ of n-butyllithium (1.6 M in hexane) are added dropwise to a mixture of 1.2 g of lithium chloride (dried beforehand under reduced pressure at 150° C.), 35 cm$^3$ of anhydrous tetrahydrofuran and 1.33 cm$^3$ of diisopropylamine, at −30° C. under an argon atmosphere. After addition, the mixture is warmed to 0° C. and then cooled again to −70° C. 50 cm$^3$ of a solution of anhydrous tetrahydrofuran containing 1 g of anhydrous pristinamycin IIA are then added over 30 minutes to the resulting mixture. The anhydrous pristinamycin IIA was obtained beforehand from a toluene/dichloromethane solution (400 cm$^3$/800 cm$^3$) containing 40 g of pristinamycin IIA, which was concentrated to dryness under reduced pressure (2.7 kPa) using a rotary evaporator over 4 hours, at a maximum of 40° C.

After stirring the reaction mixture for 5 minutes at −70° C., 1.18 cm$^3$ of methyl iodide are rapidly added. The mixture is stirred for 1 hour at −70° C. and then heated to −30° C. 2 cm$^3$ of acetic acid are then added; the temperature of the reaction mixture is allowed to rise to 0° C. and 50 cm$^3$ of water are then added. The organic phase is separated out and the aqueous phase is extracted with twice 50 cm$^3$ of ethyl acetate. The combined organic phases are washed with 50 cm$^3$ of brine and then dried over sodium sulfate, filtered and concentrated to dryness under reduced pressure (2.7 kPa) to give 1 g of a brown oil, which is purified by crystallization from 15 cm$^3$ of methyl isobutyl ketone. The solid obtained is filtered off, washed with diethyl ether and then dried at atmospheric pressure to give 0.4 g of 20-methylpristinamycin IIA in the form of white crystals melting at about 148° C.

EXAMPLE 7

(16R)-16-Deoxo-16-hydroxy-20-methylpristinamycin IIB

A solution of 3 g of anhydrous (16R)-16-deoxo-16-hydroxypristinamycin IIB and 200 cm$^3$ of anhydrous tetrahydrofuran is added over 45 minutes to 15.6 cm$^3$ of commercial lithium diisopropylamide (2 M in a THF/heptane/ethylbenzene mixture) at −71° C. under an argon atmosphere. After addition, the green-blue reaction mixture is stirred for 10 minutes at −71° C., followed by addition over 25 minutes of a solution of 0.42 cm$^3$ of methyl iodide in 20 cm$^3$ of anhydrous tetrahydrofuran, at −75° C. After addition, the mixture is stirred for 1 hour at −70° C. and then poured into a mixture of 400 cm$^3$ of water and 42 cm$^3$ of aqueous 10% phosphoric acid solution. The mixture obtained is extracted with 3 times 150 cm$^3$ of ethyl acetate. The combined organic phases are washed with 200 cm$^3$ of brine, dried over sodium sulfate, filtered and then concentrated to dryness under reduced pressure (2.7 kPa) to give a residue, which is purified by preparative HPLC [Kromasil C8, 10 μm; eluent: water/acetonitrile (70/30 by volume)]. The fractions containing the expected product are concentrated under reduced pressure (2.7 kPa) to give an aqueous phase, which is saturated with salt and then extracted with ethyl acetate. The organic phase is dried over sodium sulfate, filtered and concentrated to dryness under reduced pressure (2.7 kPa) at 40° C. to give 0.27 g of (16R)-16-deoxo-16-hydroxy-20-methylpristinamycin IIB in the form of a white solid melting starting from 131° C. The anhydrous (16R)-16-deoxo-16-hydroxypristinamycin IIB was obtained beforehand from a toluene solution (300 cm$^3$) containing 20 g of (16R)-16-deoxo-16-hydroxypristinamycin IIB, which was concentrated to dryness under reduced pressure (2.7 kPa) using a rotary evaporator, at a maximum of 40° C. The residue was dried under reduced pressure (2.7 kPa) to give 19.5 g of anhydrous (16R)-16-deoxo-16-hydroxypristinamycin IIB.

(16R)-16-Deoxo-16-hydroxypristinamycin IIB may be obtained in the following manner:

A suspension of 11.35 g of sodium borohydride in 550 cm³ of dichloromethane is refluxed for 20 minutes. 68.6 cm³ of acetic acid are then added dropwise over about 30 minutes, followed by a solution (predried over sodium sulfate) of 52.75 g of pristinamycin IIB in 230 cm³ of dichloromethane over about 45 minutes. The reaction mixture is stirred at reflux for 4.5 hours and then at 20° C. for 16 hours. 500 cm³ of dichloromethane and 1 500 cm³ of water are then added to the reaction mixture. The organic phase is separated out after settling of the phases, and the aqueous phase is extracted with 500 cm³ of methylene chloride. The organic phases are combined and the pH is adjusted to 8 by slow addition of 1 000 cm³ of saturated aqueous sodium bicarbonate solution. The resulting organic phase is washed successively with 1 000 cm³ of water and 1 000 cm³ of saturated aqueous sodium chloride solution and then treated with black 3S, dried over sodium sulfate, filtered through Celite® and concentrated to dryness under reduced pressure (2.7 kPa) to give 50 g of a pale yellow solid. 378 cm³ of aqueous 0.5 M ammonium hydroxide solution are added to a solution of the above solid in 900 cm³ of methylene chloride at 20° C. After stirring at 20° C. for 16 hours, the organic phase is separated out after settling of the phases, washed with 1 000 cm³ of water and then with 1 000 cm³ of saturated aqueous sodium chloride solution, dried over sodium sulfate, filtered and concentrated to dryness under reduced pressure (2.7 kPa) to give 46 g of a pale yellow solid, which is purified by flash chromatography [eluent: methylene chloride/methanol gradient (98/2 and then 97/3 by volume)]. After concentrating the fractions, 8.57 g of (16R)-16-deoxo-16-hydroxypristinamycin IIB are obtained in the form of an off-white foam melting at about 140° C. (dec.).

1H NMR spectrum (400 MHz, $CDCl_3$, δ in ppm): 0.96 (d, J=6.5 Hz: 3H); 1.00 (d, J=6.5 Hz: 3H); 1.10 (d, J=6.5 Hz: 3H); from 1.70 to 2.05 (mt: 6H); 1.81 (s: 3H); from 2.05 to 2.20 (mt: 2H); 2.76 (mt: 1H); 2.84 (dd, J=16 and 5.5 Hz: 1H); 3.00 (dd, J=16 and 7 Hz: 1H); 3.04 (d, J=4 Hz: 1H); 3.45 (ddd, J16–9 and 4 Hz: 1H); 3.90 (mt: 1H); 4.04 (mt: 1H); 4.27 (mt: 1H); 4.48 (ddd, J=16–9 and 4 Hz: 1H); 4.80 (dd, J=10 and 2 Hz: 1H); 4.84 (dd, J=9 and 3.5 Hz: 1H); 4.88 (mt: 1H); 5.44 (broad d, J=9 Hz: 1H); 5.67 (ddd, J=16–9 and 4 Hz: 1H); 5.80 (dd, J=16 and 1.5 Hz: 1H); 5.95 (dd, J=9 and 4 Hz: 1H); 6.19 (broad d, J=16 Hz: 1H); 6.53 (dd, J=16 and 5 Hz: 1H); 8.16 (s: 1H).

EXAMPLE 8

(16R)-16-Deoxo-16-methoxy-20-methylpristinamycin IIB

Working according to the methods described in the preceding examples, starting with (16R)-16-deoxo-16-methoxypristinamycin IIB, (16R)-16-deoxo-16-methoxy-20-methylpristinamycin IIB is prepared in the form of a pale yellow solid melting starting from 145° C.

1H NMR spectrum (300 MHz, $CDCl_3$, δ in ppm): 0.97 (d, J=6.5 Hz: 3H); 1.03 (d, J=6.5 Hz: 3H); 1.11 (d, J=6.5 Hz: 3H); from 1.70 to 2.20 (mt: 7H); 1.83 (s: 3H); 2.55 (s: 3H); 2.71 (dd, J=16 and 8.5 Hz: 1H); 2.76 (mt: 1H); 3.11 (dd, J=16 and 4 Hz: 1H); 3.42 (s: 3H); 3.55 (ddd, J=16–8.5 and 3.5 Hz: 1H); from 3.70 to 3.90 (mt: 2H); 3.97 (mt: 1H); 4.45 (ddd, J=16–8 and 4 Hz: 1H); from 4.65 to 4.85 (mt: 3H); 5.44 (broad d, J=9 Hz: 1H); 5.72 (ddd, J=16–8.5 and 4 Hz: 1H); 5.82 (dd, J=16 and 1.5 Hz: 1H); 5.94 (mt: 1H); 6.22 (broad d, J=16 Hz: 1H); 6.53 (dd, J=16 and 5 Hz: 1H).

(16R)-16-Deoxo-16-methoxy-20-methylpristinamycin IIB may be prepared as described in patent application FR 0 016 803.

The present invention also relates to pharmaceutical compositions containing at least one streptogramin derivative according to the invention, in pure form, combined with at least one group B streptogramin derivative, where appropriate in salt form, and/or in the form of a combination with one or more compatible and pharmaceutically acceptable diluents or adjuvants.

The compositions according to the invention may be used orally, parenterally, topically, rectally or as aerosols.

Solid compositions for oral administration that may be used include tablets, pills, gel capsules, powders or granules. In these compositions, the active product according to the invention, generally in the form of a combination, is mixed with one or more inert diluents or adjuvants, such as sucrose, lactose or starch. These compositions may comprise substances other than diluents, for example a lubricant such as magnesium stearate or a coating intended for sustained release.

Liquid compositions for oral administration that may be used include pharmaceutically acceptable solutions, suspensions, emulsions, syrups and elixirs containing inert diluents such as water or liquid paraffin. These compositions may also comprise substances other than diluents, for example wetting, sweetening or flavoring products.

The compositions for parenteral administration may be sterile solutions or emulsions. Solvents or vehicles that may be used include propylene glycol, a polyethylene glycol, plant oils, in particular olive oil, and injectable organic esters, for example ethyl oleate. These compositions may also contain adjuvants, in particular wetting agents, isotonic agents, emulsifiers, dispersants and stabilizers.

Sterilization may be carried out in several ways, for example using a bacteriological filter, by irradiation or by heating. They may also be prepared in the form of sterile solid compositions that may be dissolved at the time of use in sterile water or any other injectable sterile medium.

The compositions for topical administration may be, for example, creams, ointments, lotions or aerosols.

The compositions for rectal administration are suppositories or rectal capsules, which contain, besides the active principle, excipients such as cocoa butter, semisynthetic glycerides or polyethylene glycols.

The compositions may also be aerosols. For use in the form of liquid aerosols, the compositions may be stable sterile solutions or solid compositions dissolved at the time of use in apyrogenic sterile water, in saline or any other pharmaceutically acceptable vehicle. For use in the form of dry aerosols intended to be inhaled directly, the active principle is finely divided and combined with a solid water-soluble diluent or vehicle with a particle size of 30 to 80 μm, for example dextran, mannitol or lactose.

In human therapy, the novel streptogramin derivatives according to the invention are particularly useful in the treatment of infections of bacterial origin. The doses depend on the desired effect and on the duration of the treatment. The physician will determine the dosage that he considers to be the most appropriate depending on the treatment, depending on the age, weight, the degree of the infection and on the other personal factors of the individual to be treated. Generally, the doses are between 0.5 and 3 g of active product in 2 or 3 administrations per day, orally or parenterally for an adult.

The example which follows illustrates a composition according to the invention.

EXAMPLE

Tablets containing a 250 mg dose of active product and having the composition below are prepared according to the usual technique:

| | |
|---|---|
| (16R)-20-bromo-16-deoxo-16-fluoropristinamycin IIA | 175 mg |
| pristinamycin IB | 75 mg |
| excipient: starch, hydrated silica, dextrin, gelatin, magnesium stearate: qs | 500 mg |

What is claimed is:

1. A group A streptogramin compound of formula (I) or a salt thereof:

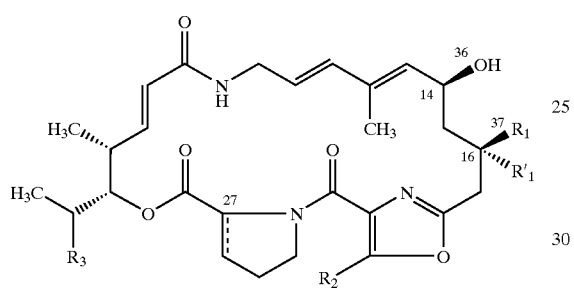

(I)

wherein:
- $R_1$ represents a halogen atom, a hydroxyl, alkyloxy, azido or thiocyanato radical, a radical —NR'R", or a radical —OR'", wherein
  - R' represents a hydrogen atom or a methyl radical;
  - R" represents a hydrogen atom, an alkyl, cycloalkyl, allyl, propynyl or benzyl radical, or a radical —NR°R°°, wherein R° and R°° each represent a methyl radical, or form, together with the nitrogen atom to which they are attached, a saturated or unsaturated 4- or 5-membered heterocycle comprising at least one hetero atom chosen from nitrogen, oxygen and sulfur, and
  - R'" represents a hydrogen atom or an alkyl, cycloalkyl, allyl, propynyl or benzyl radical; and
- $R'_1$ represents a hydrogen atom, or
- $R_1$ and $R'_1$ together form an oxo radical,
- $R_2$ represents a halogen atom, an alkyl, alkenyl, alkynyl, phenyl or heteroaryl radical, or an alkylthio, phenylthio or heteroarylthio radical, wherein said heteroaryl radical is chosen from pyridyl, thienyl, furyl, pyrrolyl, imidazolyl, pyrazinyl, quinolyl, isoquinolyl, indolyl, oxazolyl, thiazolyl, pyrazolyl, indazolyl, thiadiazolyl or oxadiazolyl,
- $R_3$ represents a hydrogen atom or a methyl or ethyl radical, and
- the bond - - - represents a single bond (27R stereochemistry) or a double bond,
- the alkyl radicals containing from 1 to 6 carbons in a straight or branched chain, the alkenyl radicals containing from 2 to 6 carbons in a straight or branched chain, and the alkynyl radicals containing from 2 to 6 carbons in a straight or branched chain.

2. A process for preparing a group A streptogramin compound according to claim 1, wherein metalation is carried out on a streptogramin compound of formula (II):

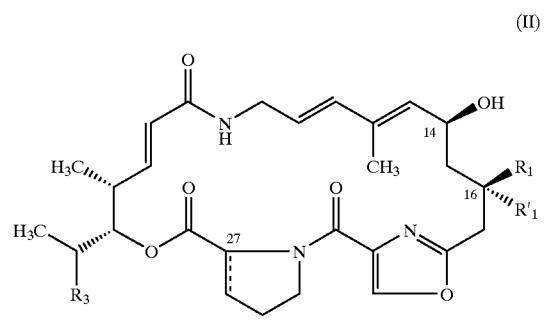

(II)

wherein
- $R'_1$, $R_3$ and the bond  are as defined in claim 1;
- $R_1$ represents a fluorine atom, a hydroxyl or alkyloxy radical, a radical —NR'R" or a radical —OR"',' wherein
  - R' represents H or a methyl radical,
  - R" represents H, an alkyl, cycloalkyl, allyl, propynyl or benzyl radical, or a radical —NR°R°°, wherein R° and R°° each represent a methyl radical, or forms together with the nitrogen atom to which they are attached, a saturated or unsaturated 4- or 5-membered heterocycle comprising at least one hetero atom chosen from nitrogen, oxygen and sulfur, and
  - R'" represents H, an alkyl, cycloalkyl, allyl, propynyl or benzyl radical; or
- $R_1$ and $R'_1$ together form an oxo radical, wherein the metalation is carried out by at least one of
  (1) the successive action of a metal amide and then by the action of an electrophilic agent represented by the formula (III):

$$R_2—X \quad \text{(III)}$$

wherein
- $R_2$ represents a halogen atom, an alkyl, alkenyl or alkynyl radical, with the proviso that $R_2$ does not represent a vinyl or ethynyl radical, and
- X represents a halogen atom, a cyano radical or a sulfonyloxy radical, or said electrophilic agent is either a halogen donor or a cyano donor; and
  (2) by the action of a disulfide when $R_2$ is alkylthio, phenylthio or heteroarylthio, wherein said heteroaryl radical is chosen from pyridyl, thienyl, furyl, pyrrolyl, imidazolyl, pyrazinyl, quinolyl, isoquinolyl, indolyl, oxazolyl, thiazolyl, pyrazolyl, indazolyl, thiadiazolyl or oxadiazolyl.

3. The process according to claim 2, wherein the electrophilic agent is chosen from at least one of (a) a halogen donor; and (b) a cyano donor.

4. A polyanion and corresponding metal counter ion, derived from corresponding group A streptogramins, depending on the nature of the substituents and depending on whether the bond - - - is a double bond or a single bond, to the structures of general formulae:

21    22
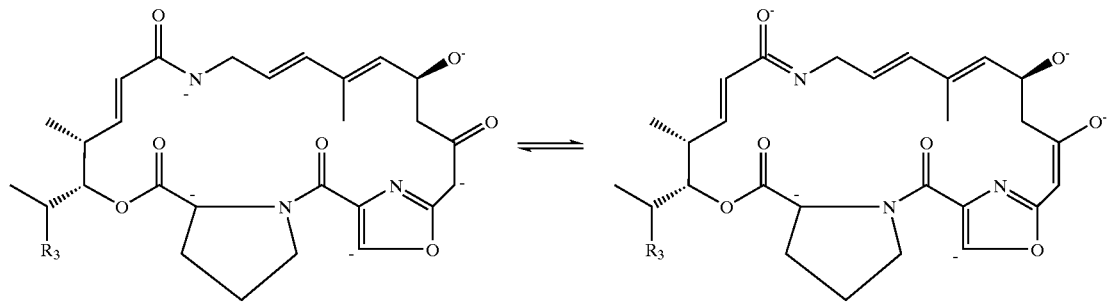
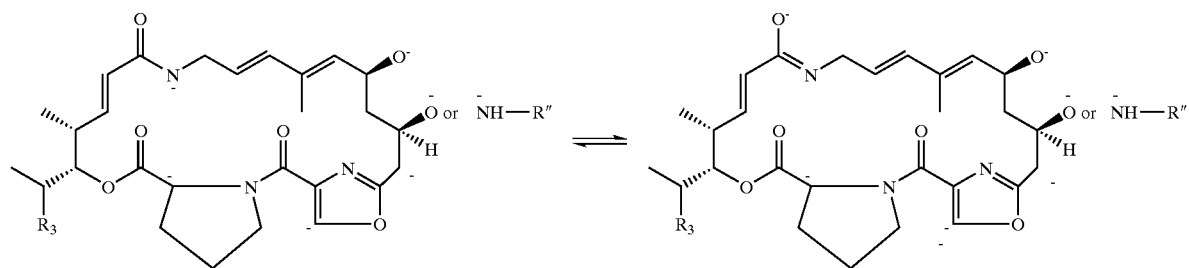
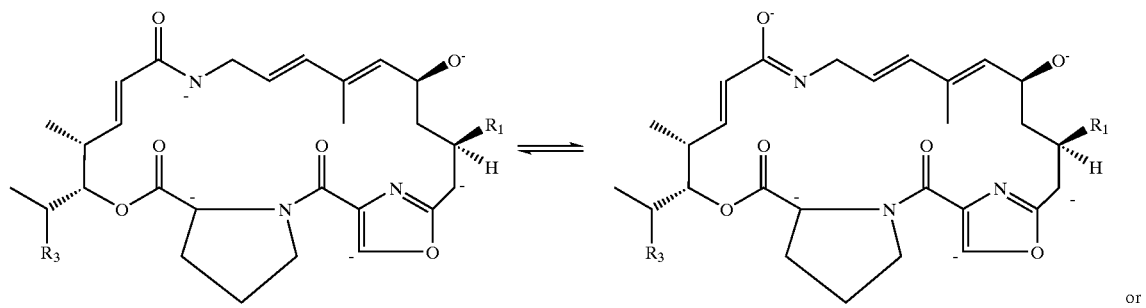
or

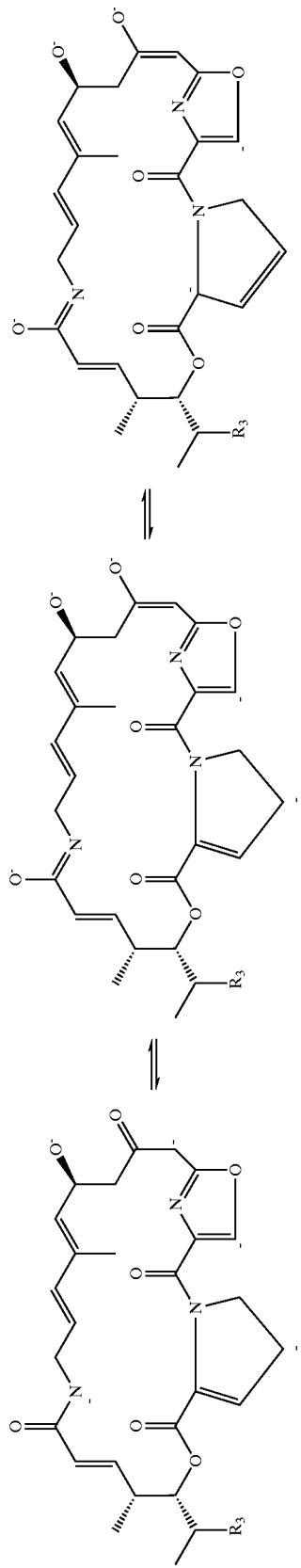
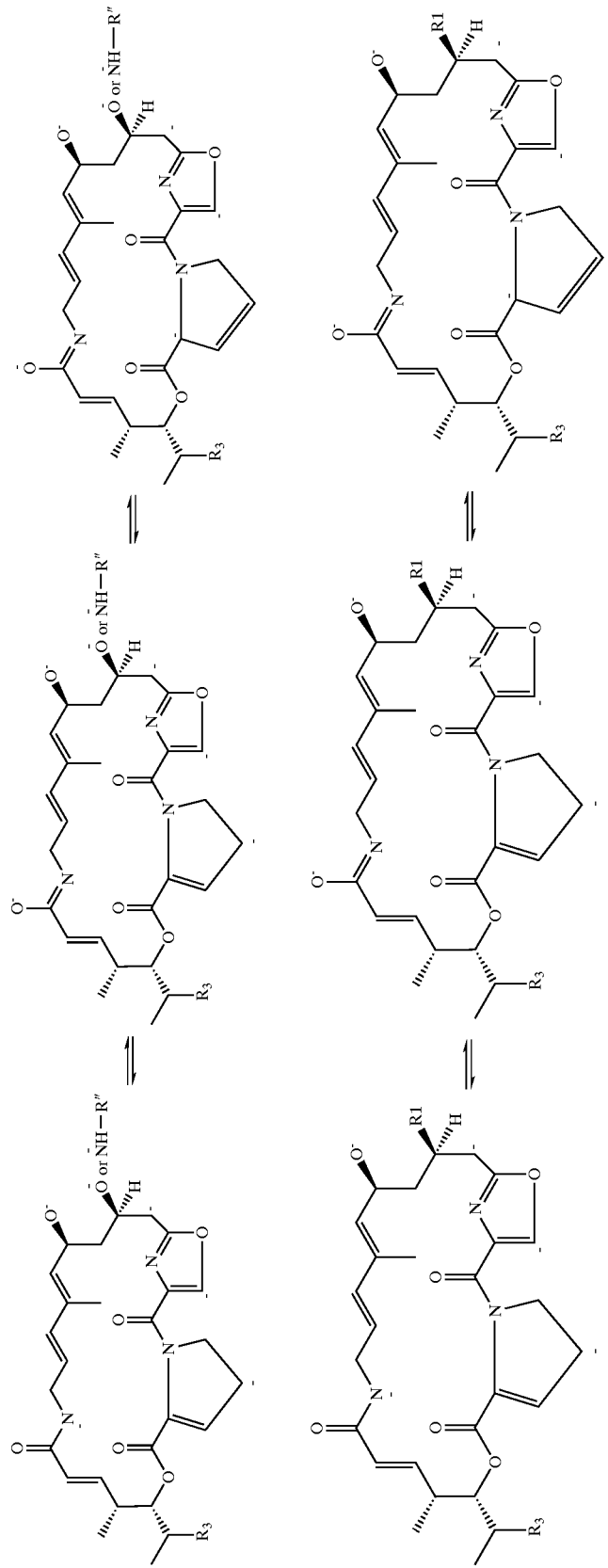

wherein
- $R_3$ represents a hydrogen atom or a methyl or ethyl radical, and
- $R_1$ represents a fluorine atom, an alkyloxy radical, a radical —NR'R", or a radical —OR''', wherein
  - R' represents a methyl radical,
  - R" represents an alkyl, cycloalkyl, allyl, propynyl or benzyl radical, or —NR°R°°, wherein R° and R°° each represent methyl, or form, together with the nitrogen atom to which they are attached, a saturated or unsaturated 4- or 5-membered heterocycle comprising at least one hetero atom chosen from nitrogen, oxygen and sulfur, and
  - R''' represents H, alkyl, cycloalkyl, allyl, propynyl or benzyl.

5. A pharmaceutical composition comprising a group A streptogramin compound according to claim 1, further comprising at least one of (i) at least one group B streptogramin, and (ii) at least one pharmaceutically acceptable diluent or adjuvant.

6. The process according to claim 2, wherein the metalation is followed by at least one conversion chosen from:

(i) conversion of said group A streptogramin compound, for which $R_2$ is a chlorine, bromine or iodine atom, into said group A streptogramin compound, for which $R_2$ is vinyl, ethynyl, phenyl or hetaroaryl radical, wherein said heteroaryl radical is chosen from pyridyl, thienyl, furyl, pyrrolyl, imidazolyl, pyrazinyl, quinolyl, isoquinolyl, indolyl, oxazolyl, thiazolyl, pyrazolyl, indazolyl, thiadiazolyl or oxadiazolyl;

(ii) conversion of said group A streptogramin compound, for which $R_1$ and $R'_1$ together form an oxo radical, into a corresponding compound for which $R_1$ is a chlorine, bromine or iodine atom or an azido or thiocyanato radical and $R'_1$ is a hydrogen atom; and (iii) conversion of said group A streptogramin compound, for which the bond --- is a double bond, into said group A streptogramin compound, for which the bond --- is a single bond.

7. The process according to claim 3, wherein the halogen donor is chosen from at least one of N-bromosuccinimide or N-chlorosuccinimide, 1,1,2,2-tetrafluoro-1,2-dichloro- or -dibromoethane, 1,2-dibromo-1,1,2,2-tetrachloroethane, 1,2-diiodoethane or 1,2-dibromoethane, 1-chloro-2-iodoethane and hexachloroacetone; and the cyano donor is chosen from tosyl cyanide.

* * * * *